(12) United States Patent
Kim et al.

(10) Patent No.: US 8,818,492 B2
(45) Date of Patent: Aug. 26, 2014

(54) APPARATUS AND METHOD FOR MEASURING GANGLION CELLS

(71) Applicant: Korea Institute of Science and Technology, Seoul (KR)

(72) Inventors: Jae Hun Kim, Seoul (KR); Seok Lee, Seoul (KR); Hyuk Jae Lee, Goyang-si (KR); Taikjin Lee, Seoul (KR); Sun Ho Kim, Seoul (KR); Seok Hwan Kim, Seoul (KR); Jin Wook Jeoung, Seoul (KR); Ki Ho Park, Seoul (KR); Ju Yeong Oh, Gimpo-si (KR); Deok Ha Woo, Seoul (KR); Chulki Kim, Samcheok-si (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 13/686,291

(22) Filed: Nov. 27, 2012

(65) Prior Publication Data
US 2014/0121530 A1    May 1, 2014

(30) Foreign Application Priority Data

Oct. 26, 2012  (KR) .......................... 10-2012-0119674

(51) Int. Cl.
*A61B 5/05*    (2006.01)
*A61B 3/14*    (2006.01)

(52) U.S. Cl.
CPC ..................................... *A61B 3/145* (2013.01)
USPC ........... 600/425; 600/558; 600/407; 600/310; 600/476; 600/477

(58) Field of Classification Search
USPC ................................. 600/407, 310, 476, 477
See application file for complete search history.

(56) References Cited

U.S. PATENT DOCUMENTS

2004/0064064 A1* 4/2004 Zhou et al. .................... 600/558
2012/0150029 A1* 6/2012 Debuc ........................... 600/425

FOREIGN PATENT DOCUMENTS

| KR | 10-2008-0013919 A | 2/2008 |
| KR | 10-2011-0054584   | 5/2011 |
| KR | 10-1092376 B1     | 12/2011 |

* cited by examiner

*Primary Examiner* — Unsu Jung
*Assistant Examiner* — Joel Lamprecht
(74) *Attorney, Agent, or Firm* — NSIP Law

(57) ABSTRACT

An apparatus for measuring ganglion cells may include: a light generation unit configured to irradiate a first light signal polarized in a first direction and a second light signal polarized in a second direction perpendicular to the first direction to a subject; a reflected light processing unit configured to generate an amplification signal corresponding to an image of the subject using a first reflection signal, which is the first light signal reflected from the subject, and a second reflection signal, which is the second light signal reflected from the subject; and an image processing unit configured to measure ganglion cells in the subject using the amplification signal. The apparatus may be used to count the number of normal ganglion cells in the retina by measuring a phase difference of two lights polarized in different directions. The apparatus may also be used to monitor the progress of glaucoma.

6 Claims, 3 Drawing Sheets

APPARATUS AND METHOD FOR MEASURING GANGLION CELLS

CROSS-REFERENCE TO RELATED APPLICATION

This application claims priority to Korean Patent Application No. 10-2012-0119674, filed on Oct. 26, 2012, and all the benefits accruing therefrom under 35 U.S.C. §119, the contents of which in its entirety are herein incorporated by reference.

BACKGROUND

1. Field

Embodiments relate to an apparatus and a method for imaging and measuring ganglion cells. More particularly, embodiments relate to an apparatus and a method for measuring ganglion cells capable of measuring number, density, etc. of ganglion cells in the retina of a human or animal eye and thus diagnosing presence and progress of diseases such as glaucoma.

2. Description of the Related Art

Glaucoma is an eye disease in which the function of the optic nerve is impaired as the optic nerve is pressed or the blood flow is restricted owing to raised intraocular pressure. The damage of the optic nerve leads to visual field loss, which over time can progress to blindness. Whereas acute glaucoma can be detected early due to severe pain, chronic glaucoma has few symptoms and, when symptoms are found, it is generally too late to treat. Accordingly, it is very important to detect glaucoma early through periodic examinations.

Since the major cause of glaucoma is damages to ganglion cells, the progress of glaucoma can be diagnosed by observing the degree of damage of the ganglion cells. The simplest method is to measure the intraocular pressure and, if it is higher than the normal intraocular pressure, treatment for glaucoma is made to lower the intraocular pressure below the normal level. For example, Korean Patent Application Publication No. 10-2011-0054584 discloses a device for measuring the intraocular pressure of a patient for diagnosis and treatment of glaucoma. However, the diagnosis based on the intraocular pressure measurement is not so accurate.

Recently, the optical coherence tomography (OCT) technique, whereby the thickness of the layer of the retina where ganglion cells are located is measured to diagnose the progress of glaucoma, is frequently used. In general, it is known that raised intraocular pressure leads to damage of the optic nerve since the optic nerve is pressed and, as a result, the ganglion cells connected to the optic nerve die and the thickness of the layer where the ganglion cells existed decreases. But, if the decreased thickness of the layer is measurable by OCT, glaucoma has already progressed a lot. Therefore, it is difficult to detect glaucoma at an early stage using this method.

SUMMARY

According to an aspect, the present disclosure provides an apparatus and a method for measuring ganglion cells, capable of measuring the number or density of ganglion cells in the retina of a human or animal eye based on phase difference measurement of two lights polarized in different directions rather than measuring the thickness of the layer where the ganglion cells are located.

According to an embodiment, an apparatus for measuring ganglion cells includes: a light generation unit configured to irradiate a first light signal polarized in a first direction and a second light signal polarized in a second direction perpendicular to the first direction to a subject; a reflected light processing unit configured to generate an amplification signal corresponding to an image of the subject using a first reflection signal, which is the first light signal reflected from the subject, and a second reflection signal, which is the second light signal reflected from the subject; and an image processing unit configured to measure ganglion cells in the subject using the amplification signal.

According to an embodiment, a method for measuring ganglion cells includes: generating a first light signal polarized in a first direction and a second light signal polarized in a second direction perpendicular to the first direction; irradiating the first light signal and the second light signal to a subject; generating an amplification signal corresponding to an image of the subject using a first reflection signal, which is the first light signal reflected from the subject, and a second reflection signal, which is the second light signal reflected from the subject; and measuring ganglion cells in the subject using the amplification signal.

In accordance with the apparatus and method for measuring ganglion cells according to embodiments, the ganglion cells in the retina may be measured by imaging the phase difference of two lights polarized in different directions. The apparatus and method for measuring ganglion cells may be used to measure the number or density of the ganglion cells in the retina of a human or animal eye and thus to diagnose the presence and progress of glaucoma.

BRIEF DESCRIPTION OF THE DRAWINGS

The above and other objects, features and advantages of the present disclosure will become apparent from the following description of certain exemplary embodiments given in conjunction with the accompanying drawings, in which.

DETAILED DESCRIPTION

Hereinafter, exemplary embodiments will be described in detail with reference to the accompanying drawings.

Figure 1:
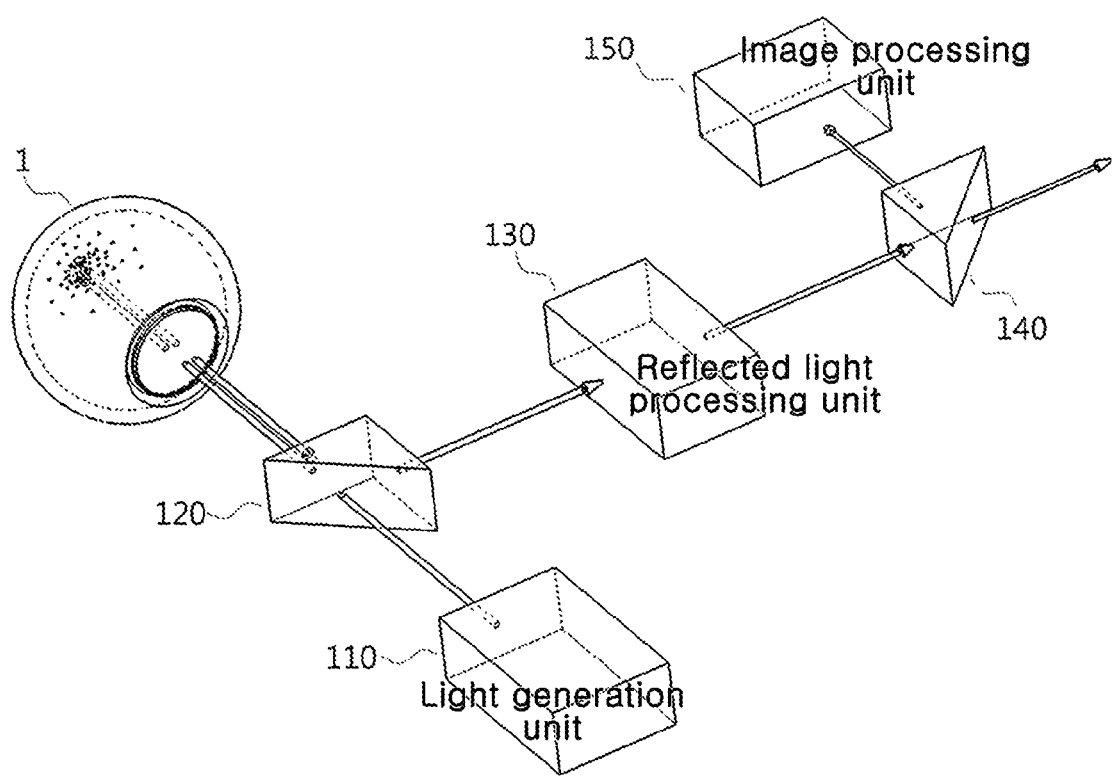
FIG. 1 is a schematic diagram showing a configuration of an apparatus for measuring ganglion cells according to an embodiment.

FIG. 1 is a schematic diagram showing a configuration of an apparatus for measuring ganglion cells according to an embodiment.

Referring to FIG. 1, an apparatus for measuring ganglion cells according to the embodiment may comprise a light generation unit 110, a reflected light processing unit 130 and an image processing unit 150. The light generation unit 110 and the reflected light processing unit 130 may respectively comprise one or more optical element for irradiating light to a subject 1 and detecting light reflected from the subject 1. The subject 1 may be a human or animal eye. And, the image processing unit 150 may measure ganglion cells present in the subject 1 using an image obtained from reflected light.

The light generation unit 110 irradiates two lights polarized in different directions to the subject 1. In an embodiment, the light generation unit 110 is configured to irradiate a first light signal and a second light signal, which are perpendicularly polarized with respect to each other to obtain a differential interference contrast (DIC) image of the subject 1.

Figure 2:
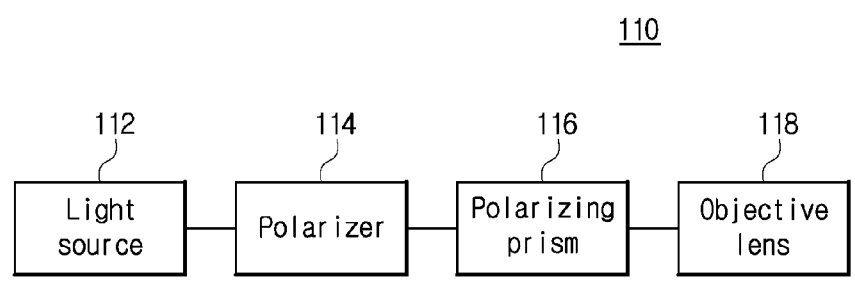
FIG. 2 is a block diagram showing a configuration of a light generation unit of an apparatus for measuring ganglion cells according to an embodiment.

FIG. 2 is a block diagram showing a configuration of the light generation unit 110 of an apparatus for measuring ganglion cells according to an embodiment.

Referring to FIG. 2, the light generation unit 110 may comprise a light source 112, a polarizer 114, a polarizing prism 116 and an objective lens 118. However, this is only exemplary and the light generation unit 110 does not necessarily comprise all the optical members 112, 114, 116, 118 shown in FIG. 2. That is to say, some members may be omitted or other additional members may be added.

The light source 112 may generate a light to observe the subject. In an embodiment, the light source 112 may be a light-emitting diode (LED), a fluorescent lamp, a mercury lamp, a sodium lamp, or the like, but is not limited thereto.

The polarizer 114 may polarized the light generated by the light source 112 in specific directions. Although the light generated by the light source 112 oscillates in all directions perpendicular to the path of the light, it is separated into lights polarized in specific directions as it passes through the polarizer 114. In an embodiment, the polarizer 114 may generate a polarization signal by separating only the light polarized with an angle of 45° from the light generated by the light source 112.

The polarizing prism 116 may separate the polarization signal transmitted from the polarizer 114 into two light signals polarized in perpendicular directions. In an embodiment, the polarizing prism 116 may be a Wollaston prism. Since the Wollaston prism consists of two layers of crystalline materials, it has different refractive indices for different polarization directions. According to Malus' law, the intensity of a polarized light is proportional to the cosine of the angle between the light's initial polarization direction and the axis of the polarizer. Thus, the light passing through the Wollaston prism is separated into a first light signal and a second light signal having perpendicular polarization directions. Detailed explanation of the Wollaston prism will be omitted since they are well known to those of ordinary skill in the art.

In an embodiment, the polarizing prism 116 may have a crystal direction having an angle of 45° from the polarization direction of the polarizer 114. By the polarizing prism 116, the polarization signal may be separated into a first light signal polarized with an angle of +45° from the initial polarization direction and a second light signal polarized with an angle of −45°. For example, if the polarizer 114 has a polarization direction with an angle of 45°, the polarization signal generated by the polarizer 114 may be separated into a first light signal polarized with an angle of 90° and a second light signal polarized with an angle of 0° as it passes through the polarizing prism 116.

However, the above-described polarization angle is given only as an example and the polarization directions of the polarization signal and the first light signal and the second light signal generated therefrom are not limited to specific angles.

The objective lens 118 may converge the first light signal and the second light signal polarized in perpendicular directions on the subject 1. In an embodiment, the objective lens 118 may be a convex lens but is not limited thereto. Owing to the characteristics of the polarizing prism 116, the first light signal and the second light signal separated by the polarizing prism 116 are not converged on the subject 1 at the perfectly same region but at adjacent regions with a slight offset.

In an embodiment, the apparatus for measuring ganglion cells may comprise a first prism 120 on the light path between the light generation unit 110 and the subject 1. The first light signal and the second light signal may be propagated through the first prism 120 and may be converged on the subject 1.

The first light signal and the second light signal may be reflected on the surface of the subject 1 and/or may be reflected after penetrating into the subject 1 by a predetermined depth. The first light signal is reflected on the subject 1 and becomes a first reflection signal, and the second light signal is reflected on the subject 1 and becomes a second reflection signal. Since the first light signal and the second light signal are irradiated to adjacent but different regions of the subject and then reflected, the lengths or refractive indices of light path of the first light signal and the second light signal become different after the reflection. The difference in light path causes phase difference of the first reflection signal and the second reflection signal. For example, of the first light signal and the second light signal, the signal reflected at a relatively thicker region may have a relative phase delay with respect to the other.

The first reflection signal and the second reflection signal reflected on the subject 1 may be reflected on the first prism 120 and incident on the reflected light processing unit 130. The reflected light processing unit 130 may generate an amplification signal corresponding to an image of the subject 1 from the first reflection signal and the second reflection signal. The reflected light processing unit 130 may convert the first reflection signal and the second reflection signal to have the same polarization direction and convert the phase difference of the first and second light signals arising as the first and second light signals passes through the subject 1 to a change in amplitude.

Figure 3:
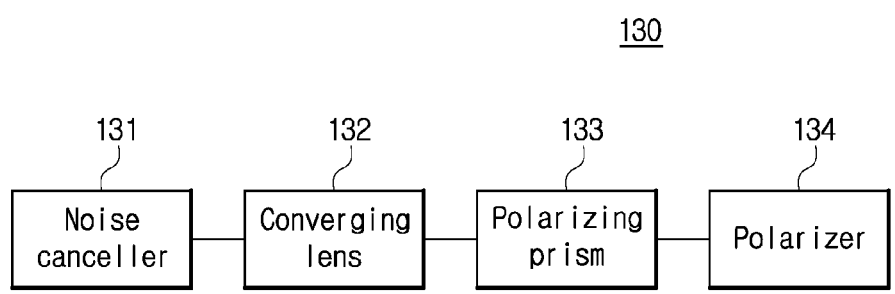
FIG. 3 is a block diagram showing a configuration of a reflected light processing unit of an apparatus for measuring ganglion cells according to an embodiment.

FIG. 3 is a block diagram showing a configuration of the reflected light processing unit 130 of an apparatus for measuring ganglion cells according to an embodiment.

Referring to FIG. 3, the reflected light processing unit 130 may comprise a noise canceller 131, a converging lens 132, a polarizing prism 133 and a polarizer 134. However, this is only exemplary and the reflected light processing unit 130 does not necessarily comprise all the optical members 131, 132, 133, 134 shown in FIG. 3. That is to say, some members may be omitted or other additional members may be added.

The noise canceller 131 may cancel a noise component from the light transmitted from the first prism 120 and extract the first reflection signal and the second reflection signal. For example, the noise component may be a reflected light component owing to the region other than the retina, e.g. the crystalline lens, from the signal included in the light reflected on the subject 1. The cancellation of the noise component may be performed by any known or to-be-developed noise processing technique, without being limited to a specific technique.

The converging lens 132 may converge the first reflection signal and the second reflection signal with the noise component cancelled by the noise canceller 131 on the polarizing prism 133. In an embodiment, the converging lens 132 may be a convex lens but is not limited thereto.

The polarizing prism 133 may combine the first reflection signal and the second reflection signal into one light having the same polarization direction so as to generate an amplification signal. In an embodiment, the polarizing prism 133 may be a Wollaston prism like the polarizing prism 116 of the light generation unit 110. For example, if the first reflection signal is polarized with an angle of 90° and the second reflection signal is polarized with an angle of 0°, the amplification signal combined therefrom by the polarizing prism 133 may have a polarization direction with an angle of 135°. The first reflection signal and the second reflection signal reflected on the subject have a phase difference. The interference owing to the phase difference leads to a change in amplitude of the amplification signal.

The amplification signal may pass through the polarizer 134 and be transmitted to the image processing unit 150. The polarizer 134 may have a polarization direction perpendicular to that of the polarizer 114 of the light generation unit 110. For example, if the polarization direction of the polarizer 114 is 45°, the polarization direction of the polarizer 134 may be 135°. The polarizer 134 may prevent the first and second light signals generated by the light generation unit 110 from being directly incident on the image processing unit 150 without being reflected on the subject. On the other hand, since the amplification signal generated from the first and second reflection signals is polarized with an angle of 135°, it may pass through the polarizer 134 and be incident on the image processing unit 150.

Since the first and second reflection signals have been reflected at the adjacent regions with a slight offset, the amplification signal generated therefrom is not a perfectly aligned single image but an overlap of two images with a slight offset. If the first light signal and the second light signal have passed through the regions of the subject having different thicknesses or refractive indices, a phase difference occurs between the first and second reflection signals and the portion having the phase difference appears brighter or darker than other portions owing to interference in the overlapped amplification signal. Accordingly, even if the subject 1 comprises a transparent material such as the retina, the image of the subject 1 exhibits contrast due to the phase difference.

The image processing unit 150 may measure ganglion cells present in the subject 1 using the amplification signal. The image processing unit 150 may observe the size and shape of the cells in the retina using the amplification signal and may count the cells that satisfy a given condition or measure a density thereof. For example, the image processing unit 150 may determine the presence or degree of glaucoma by measuring the number or density of normal ganglion cells in the retina. The measuring of the number or density of the cells by the image processing unit 150 may be performed by any known or to-be-developed image processing technique, without being limited to a specific technique.

In an embodiment, the apparatus for measuring ganglion cells may comprise a second prism 140 on the light path between the reflected light processing unit 130 and the image processing unit 150. Part of the amplification signal generated by the reflected light processing unit 130 may be reflected on the second prism 140 and incident on the image processing unit 150. Meanwhile, another part of the amplification signal generated by the reflected light processing unit 130 may pass through the second prism 140 and be transmitted to an external image observation device (not shown). For example, the image of the subject 1 generated from the amplification signal may be transmitted to the external image observation device with predetermined time intervals or upon the request of a user. Also, the image may be provided, for example, together with the number of the cells in the layer of the ganglion cells through software processing similar to that performed by the image processing unit 150.

Using the apparatus for measuring ganglion cells according to embodiments, it is possible to observe the subject through an image generated using two reflected lights having different polarization directions, using contrast in the image generated from interference caused by the phase difference. For example, the apparatus for measuring ganglion cells may be used to measure the number or density of normal ganglion cells present in the retina and thus to diagnose the presence and progress of glaucoma.

Since it is possible to observe the ganglion cells using the apparatus for measuring ganglion cells according to embodiments, it is possible to directly monitor the decrease of ganglion cells due to glaucoma. This is distinguished from the conventional optical coherence tomography (OCT) technique wherein the thickness of the layer where the ganglion cells are located is measured, not the individual ganglion cells. Accordingly, the apparatus for measuring ganglion cells according to embodiments allows diagnosis of glaucoma at an earlier stage as compared to the conventional OCT-based measurement.

Further, the apparatus for measuring ganglion cells according to embodiments is not limited to the diagnosis of glaucoma but is also applicable to other diseases of the retina. And, the apparatus for measuring ganglion cells according to embodiments may be used as an auxiliary apparatus during surgery. For example, the apparatus for measuring ganglion cells may be used to image retinal cells and the imaged retinal cells may be used as marker during surgery. In addition, the apparatus for measuring ganglion cells may be used to monitor the progress of retinal diseases and investigate the diseases in cellular level using images.

Hereinafter, a method for measuring ganglion cells according to an embodiment will be described. A method for measuring ganglion cells according to the embodiment may be performed using the apparatus for measuring ganglion cells described above referring to FIGS. 1 through 3.

A first light signal polarized in a first direction and a second light signal polarized in a second direction perpendicular to the first direction may be generated. For example, a polarizer may be used to polarize a light in one direction and the light that has passed through the polarizer may be passed through a Wollaston prism to generate a first light signal and a second light signal having perpendicular polarization directions. The generated first light signal and second light signal may be irradiated to a subject and reflected on the surface of the subject and/or may be reflected after penetrating into the subject by a predetermined depth An amplification signal corresponding to an image of the subject may be generated using a first reflection signal, which is the first light signal reflected from the subject, and a second reflection signal, which is the second light signal reflected from the subject. In an embodiment, a noise component may be cancelled from the light reflected on the subject and the first reflection signal and the second reflection signal may be extracted. An amplitude of the amplification signal may be determined based on interference caused by a phase difference of the first reflection signal and the second reflection signal.

Then, ganglion cells present in the subject may be measured using the amplification signal. For example, the number or density of normal ganglion cells in the human or animal retina may be measured to diagnose the presence and progress glaucoma.

While the present disclosure has been described with respect to the specific embodiments, it will be apparent to those skilled in the art that various changes and modifications may be made without departing from the spirit and scope of the disclosure as defined in the following claims.

What is claimed is:

1. An apparatus for measuring ganglion cells, the apparatus comprising:
 a light generation unit configured to irradiate a first light signal and a second light signal to adjacent regions of a subject with an offset, the first light signal being polarized in a first direction and the second light signal being polarized in a second direction perpendicular to the first direction;
 a reflected light processing unit configured to generate an amplification signal corresponding to an image of the subject using a phase difference of a first reflection signal and a second reflection signal, wherein the first signal corresponds to the first light signal being reflected from the subject and the second reflection signal corresponds to the second light signal being reflected from the subject; and an image processing unit configured to measure ganglion cells in the subject using the amplification signal.

2. The apparatus for measuring ganglion cells according to claim 1, wherein the image processing unit is configured to measure a number or density of the ganglion cells.

3. The apparatus for measuring ganglion cells according to claim 1, wherein the light generation unit comprises:

a polarizer polarizing a light in one direction; and a polarizing prism generating a first light and a second light to be polarization-rotated by the ganglion cell from the light that has passed through the polarizer.

4. A method for measuring ganglion cells, comprising:

generating a first light signal polarized in a first direction and a second light signal polarized in a second direction perpendicular to the first direction;

irradiating the first light signal and the second light signal to adjacent regions of a subject with an offset;

generating an amplification signal corresponding to an image of the subject using a phase difference of a first reflection signal and a second reflection signal, wherein the first reflection signal corresponds to the first light signal be reflected from the subject and a the second reflection signal corresponds to the second light signal being reflected from the subject; and measuring ganglion cells in the subject using the amplification signal.

5. The method for measuring ganglion cells according to claim 4, wherein said measuring the ganglion cells comprises measuring a number or density of the ganglion cells.

6. The method for measuring ganglion cells according to claim 4, wherein said generating the amplification signal comprises cancelling a noise component from the light reflected on the subject so as to extract the first reflection signal and the second reflection signal to form the image of ganglion cells.

\* \* \* \* \*